United States Patent
Kopperschmidt et al.

(10) Patent No.: US 8,439,857 B2
(45) Date of Patent: May 14, 2013

(54) METHOD AND DEVICE FOR RECOGNITION OF PARAVASAL BLEEDING

(75) Inventors: Pascal Kopperschmidt, Dittelbrunn (DE); Malte Gross, Ulm (DE); Reiner Spickermann, Wasserlosen-Burghausen (DE)

(73) Assignee: Fresenius Medial Care Deutschland GmbH, Bad Homburg (DE)

( * ) Notice: Subject to any disclaimer, the term of this patent is extended or adjusted under 35 U.S.C. 154(b) by 48 days.

(21) Appl. No.: 13/130,116

(22) PCT Filed: Nov. 14, 2009

(86) PCT No.: PCT/EP2009/008128
§ 371 (c)(1),
(2), (4) Date: May 19, 2011

(87) PCT Pub. No.: WO2010/057600
PCT Pub. Date: May 27, 2010

(65) Prior Publication Data
US 2011/0230812 A1    Sep. 22, 2011

(30) Foreign Application Priority Data
Nov. 19, 2008  (DE) .......................... 10 2008 057 994

(51) Int. Cl.
*A61M 37/00* (2006.01)
*A61B 5/02* (2006.01)

(52) U.S. Cl.
USPC ......................................... 604/4.01; 600/481

(58) Field of Classification Search ....................... None
See application file for complete search history.

(56) References Cited

U.S. PATENT DOCUMENTS

| | | | |
|---|---|---|---|
| 4,846,792 A | 7/1989 | Bobo et al. | |
| 5,423,743 A | 6/1995 | Butterfield | |
| 7,172,570 B2 * | 2/2007 | Cavalcanti et al. | 604/6.11 |
| 2001/0007930 A1 * | 7/2001 | Kleinekofort | 604/4.01 |
| 2009/0292236 A1 | 11/2009 | Kleinekofort | |

FOREIGN PATENT DOCUMENTS

| | | |
|---|---|---|
| DE | 102 54 988 | 6/2004 |
| DE | 10 2006 032 815 | 1/2008 |
| EP | 0 995 451 | 4/2000 |
| EP | 1 399 204 | 3/2004 |
| EP | 1 930 035 | 6/2008 |
| WO | WO 2005/105182 | 11/2005 |

OTHER PUBLICATIONS

International Preliminary Report on Patentability for PCT/EP2009/008128 mailed on May 31, 2011. PCT International Search Report for PCT/EP2009/008128 mailed on Mar. 4, 2010.

* cited by examiner

*Primary Examiner* — Melanie J Hand
*Assistant Examiner* — Andrew S Lo
(74) *Attorney, Agent, or Firm* — Kenyon & Kenyon LLP

(57) ABSTRACT

A method and a device for recognition of paravasal bleeding upon a supplying of blood to a vascular access via a line and/or upon the removal of blood from a vascular access via a line is provided. A device for extracorporeal blood treatment comprising a device for recognition of paravasal bleeding is also provided. The method and the device are based on the change of arterial pressure in the arterial branch or the venous pressure in the venous branch of the extra-corporeal circuit being registered during the extracorporeal blood treatment. One aspect of the method and the device is that pressure changes that come from a pressure level exhibiting a large difference from a reference value are more strongly considered than those that come from a pressure level that exhibits only a minor difference from the reference value.

26 Claims, 2 Drawing Sheets

METHOD AND DEVICE FOR RECOGNITION OF PARAVASAL BLEEDING

CROSS REFERENCE TO RELATED APPLICATIONS

This is a 371 national phase application of PCT/EP2009/008128 filed Nov. 14, 2009, which claims priority from German Patent Application No. DE 10 2008 057 994.7, filed Nov. 19, 2008.

FIELD OF THE INVENTION

The present invention relates to a method and arrangement for detecting perivascular bleeding when blood is being fed to a vascular access via a line and/or when blood is being taken from a vascular access via a line, and in particular perivascular bleeding during extra-corporeal blood treatment, such for example as for the purposes of hemodialysis, hemofiltration or hemodiafiltration. As well as this, the present invention also relates to an apparatus for extra-corporeal blood treatment, in particular for the purposes of hemodialysis, hemofiltration or hemodiafiltration, which has an arrangement for detecting perivascular bleeding.

BACKGROUND

Arrangements for feeding blood to a vascular access and/or for taking blood from a vascular access, via a line, are generally familiar. Such arrangements are distinguished by the fact that the blood is fed to the vascular access, such for example as an access to a vein or artery, or is taken away from the vascular access, via a line. Arrangements of this kind are known in the form of, for example, infusion or transfusion arrangements.

The known pieces of apparatus for extra-corporeal blood treatment, for the purposes of hemodialysis, hemofiltration or hemodiafiltration for example, are also arrangements in which blood is fed to a vascular access via a line and blood is taken from a vascular access via a line.

In the known methods of treating blood, such as for hemodialysis, hemofiltration or hemodiafiltration for example, the patient's blood is conveyed through an extra-corporeal blood circuit which includes the means for treating the blood. The extra-corporeal blood circuit is generally fitted with a protective system which constantly monitors the arterial and venous pressures in the circuit. The purpose of this monitoring of pressure is to detect various complications which may occur during the extra-corporeal blood treatment. Among the possible complications is a faulty vascular access which is attributable to, for example, the needle slipping out or being drawn in.

When a faulty vascular access is found, the known protective systems as a rule make provision for the blood pump for pumping the blood in the extra-corporeal blood circuit to be stopped, a tube clamp on the venous blood line of the extra-corporeal circuit to be closed and an audio or visual warning signal to be given. By this means, the blood treating apparatus is changed to a state which is safe for the patient, but one which results in the therapy being interrupted.

Methods and arrangements for monitoring an extra-corporeal blood circuit which are based on monitoring of the pressure in both the venous and the arterial segments of the extra-corporeal blood circuit are known for example from German Patent Application Publication DE 10 2006 032 815 A1 and European Patent Application Publication EP 0 995 451 A2.

A further complication which may occur in the course of, for example, extra-corporeal blood treatment is an injury to the vascular access which results in bleeding into the surrounding tissue, something which is also referred to as perivascular bleeding. Because cases of perivascular bleeding produce only a very slow rise in pressure in the line running to the puncture needle or in the puncture needle itself, the detection of perivascular bleeding is a problem in practice. If the pressure in the line or needle is still well below the limiting value of pressure at which the known pressure-monitoring arrangements respond, the rise in pressure per unit of time, which is only small, is not noticed at first, even though more and more blood is continuously bleeding into the tissue at the time and builds up there when this happens, as a result of which more and more harm is done to the patient. A considerable amount of time therefore passes, in which blood bleeds into the tissue undetected, until the limiting level of pressure is reached.

Other methods and arrangements for detecting a vascular access which is not in good order and which are based on the monitoring of pressure signals are known from, for example, U.S. Pat. No. 4,530,696, U.S. Pat. No. 5,423,743 or U.S. Pat. No. 4,846,792. Known from European Patent EP 0 817 653 B1 is an arrangement which is fitted to a puncture needle to detect the entry of blood into the needle. The entry of blood when the blood vessel is pierced is detected by measuring a rise in pressure by means of a pressure sensor. With the known arrangement, it is even possible for the piercing of the opposite wall of the vessel to be detected by means of the drop in pressure which occurs when the opposite wall of the vessel is pierced.

The object underlying the present invention is to specify a method which, when blood is being fed to a vascular access via a line and/or blood is being taken from a vascular access via a line, and in particular in extra-corporeal blood treatment, makes it possible for perivascular bleeding to be detected quickly with relatively high safety and reliability. A further object of the present invention is to provide an arrangement for detecting perivascular bleeding which, when blood is being fed to a vascular access and/or blood is being taken from a vascular access, and in particular in extra-corporeal blood treatment, allows perivascular bleeding to be detected quickly with relatively high safety and reliability. As well as this, it is also an object of the present invention to specify an extra-corporeal blood treating apparatus having an arrangement for detecting perivascular bleeding which detects perivascular bleeding quickly with relatively high safety and reliability.

These objects are achieved in accordance with the present invention by virtue of the features of features described herein.

SUMMARY

The basic principle of the present invention is that continuous increases in pressure which begin at a level of pressure which is well below the limiting value of pressure which is laid down in the case of the known monitoring arrangements are taken account of in disproportionate manner with the help of an analyzing algorithm for the dynamic analysis of pressure, the reason being that, when there are initial states of this kind, the danger exists of perivascular bleeding continuing for a particularly long time before they are detected by means of the known monitoring arrangements.

Because changes in pressure which are a long way away from the preset reference value are intended to make a larger contribution to the analysis, the value of a suitable non-linear function of the difference between the pressure measured and a preset reference value is determined in accordance with the present invention. Basically, any non-linear function may be used which supplies larger contributions for high absolute values of the difference between the pressure measured and a preset reference value than for small absolute values of the difference between the pressure measured and a preset reference value. A power function may be used for example, the difference between the pressure measured and a preset reference value being raised to a higher power for example. As a particular preference, the absolute value of the difference between the pressure measured and the preset reference value may be raised to a higher power. It has been found in practice that the absolute value of the difference between the pressure measured and a preset reference value should be raised to a power in the range of values from 2 to 4. The exponent does not need to be 2, 3 or 4 in this case and basically the exponent may be any desired intermediate value in the specified range of values from 2 to 4. What was found particularly advantageous in laboratory tests was the power of three. The higher the value of the power, the larger are the contributions made by changes in pressure a long way away from the reference value.

In the event that the value of the non-linear function exceeds a preset limiting value, it is concluded that there is perivascular bleeding.

In extra-corporeal blood treatment, the method according to the present invention and the arrangement according to the present invention are based on the change in arterial pressure being detected in the arterial segment and/or the change in venous pressure being detected in the venous segment. If perivascular bleeding occurs during blood treatment, it is found that the positive back-pressure in the line which runs to the vascular access, i.e. at the venous needle, rises, or the suction pressure in the line running away from the vascular access, i.e. at the arterial needle, rises, i.e. the suction pressure becomes more negative. Initially the rise in pressure begins moderately and then becomes increasingly large. It is therefore crucial to the method according to the present invention and the arrangement according to the present invention for greater account to be taken of changes in pressure which start from a level of pressure which is a long distance away from the reference value than of ones which start from a level of pressure which is only a short distance away from the reference value.

The method according to the present invention and the arrangement according to the present invention are able to monitor not only the pressure at the venous needle of an extra-corporeal blood treating apparatus but, similarly, the pressure too at the arterial needle of the extra-corporeal blood treating apparatus, in order for example to enable a puncture needle which is drawn in against the wall of the blood vessel to be detected.

The method according to the present invention and the arrangement according to the present invention are able to make use of the arterial and venous pressure sensors which are present anyway in known pieces of blood treating apparatus. The change on the apparatus side to allow the protective system to be implemented is therefore confined simply to a modification of the control system of the apparatus.

In a preferred embodiment of the present invention, the integral of the value of the power of the absolute value of the difference between the pressure measured and the preset reference value is determined over a preset interval of time $t_2-t_1$, and is compared with the preset arterial or venous limiting value on the exceeding of which it is concluded that there is perivascular bleeding. The differences are thus summed until the value of the integral exceeds a critical value.

The method according to the present invention and the arrangement according to the present invention may also be combined with other methods and arrangements for detecting a faulty vascular access in extra-corporeal blood treatment. The safety and reliability of the monitoring system can be increased still further in this way. The method according to the present invention and the arrangement according to the present invention may for example be combined with the methods and arrangements which are disclosed in German Patent Application Publication DE 10 2006 032 815 A1 and European Patent Application Publication EP 0 995 451 A2.

The intention is not for the conventional monitoring of the arterial or venous pressure in the known pieces of blood treating apparatus to be superseded by the monitoring of difference according to the present invention and instead the two monitoring systems may operate independently of one another.

When there are continuous increases in pressure due to perivascular bleeding which start from a level of pressure which is below but close to the upper limiting value of pressure of the conventional pressure monitoring system, the conventional pressure monitoring system will react after only a short time to the known upper limiting value of pressure being exceeded. It is not therefore necessary for account to be taken in a disproportionate manner of increases in pressure which start from such a level of pressure because there is no danger of increases in pressure of this kind remaining unnoticed for any length of time. When there are continuous increases in pressure due to perivascular bleeding which start from a level of pressure which is well below the upper limiting value of pressure of the conventional pressure monitoring system, disproportionately larger contributions to the integral are calculated in accordance with the present invention, and it can thus be concluded that there is perivascular bleeding at an early stage.

In the event of perivascular bleeding occurring, an audio and/or visual alarm is preferably given. As well as this, the flow of blood in the extra-corporeal blood circuit may also be interrupted to prevent blood from being lost. The flow of blood may be interrupted in the known pieces of apparatus for extra-corporeal blood treatment by stopping the blood pump which is arranged in the extra-corporeal blood circuit and/or closing a safety value which is arranged in the extra-corporeal blood circuit, such as a tube clamp for example and in particular the venous tube clamp which is arranged on the venous blood line.

The method according to the present invention and the arrangement according to the present invention are basically suitable for detecting the unintentional, accidental infusion of blood into the tissue of a patient surrounding a blood vessel as a result of the accidental piercing of the opposite wall of the blood vessel. In particular, the method according to the present invention and the arrangement according to the present invention are suitable for use in all the methods of extra-corporeal blood treatment in which blood is fed back into a blood vessel of the patient via a needle. Examples of these are hemodialysis, hemofiltration or hemodiafiltration and also methods of cell separation in which a patient's blood is subjected to cell separation in an extra-corporeal blood circuit and is separated into its constituent parts when this is done.

In what follows, the present invention will be explained in detail by taking extra-corporeal blood treatment as an example and by reference to the drawings. The method according to the present invention and the arrangement according to the present invention for detecting perivascular bleeding in extra-corporeal blood treatment, and the extra-corporeal blood treating apparatus according to the present invention having the arrangement for detecting perivascular bleeding, will be described in detail by reference to an embodiment. Basically however the present invention may also be applied to any other accesses to a patient's vascular system.

DETAILED DESCRIPTION

Figure 1:
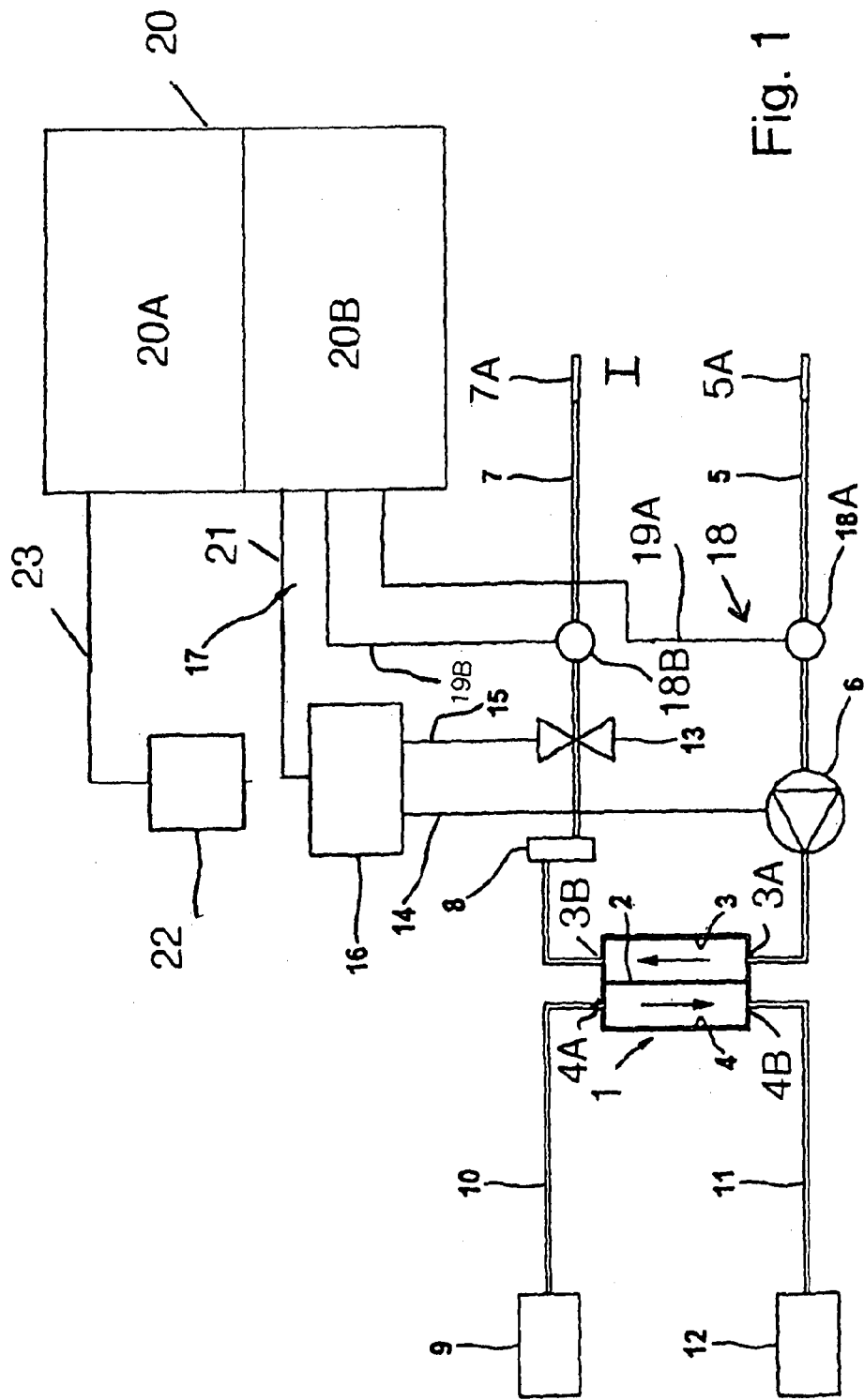
FIG. 1 is a highly simplified schematic view of an apparatus for extra-corporeal blood treatment which has an arrangement for detecting perivascular bleeding.

FIG. 1 is a highly simplified schematic view of a dialysis apparatus as an embodiment of extra-corporeal blood treating apparatus.

The dialysis apparatus has, as a blood treating means, a dialyzer 1 which is divided by a semi-permeable membrane 2 into a blood chamber 3 and a dialysis-fluid chamber 4. Connected to the inlet 3A of the blood chamber 3 is an arterial blood line 5 into which a peristaltic blood pump 6 is connected. From the outlet 3B of the blood chamber 3, a venous blood line 7 runs to the patient. Connected into the venous blood line 7 is a drip chamber 8. Connected to the ends of the arterial and venous blood lines 5, 7 are needles 5A and 7A which are respectively inserted in appropriate arterial and venous blood vessels (shunts) of the patient. The arterial and venous blood lines 5, 7 form the arterial and venous segments, respectively, of the extra-corporeal blood circuit I. The blood lines are part of a system of flexible tubing which is designed to be disposable and which is inserted in the dialysis apparatus.

Fresh dialysis fluid is made available in a source of dialysis fluid 9. From the source of dialysis fluid 9, a dialysis-fluid infeed line 10 runs to the inlet 4A of the dialysis-fluid chamber 4A of the dialyzer 1, while a dialysis-fluid takeaway line 11 runs from the outlet 4B of the dialysis chamber 4 to a discharge 12.

The dialysis apparatus also has other components, such for example as a status-assessing means and an ultrafiltration means, but for the sake of greater clarity these have not been shown.

As well as this, the dialysis apparatus also has means for interrupting the flow of blood in the event of a faulty vascular access. To interrupt the flow of blood, a shut-off clamp 13 which is electromagnetically operated is provided on the venous blood line 7 downstream of the drip chamber 8. The arterial blood pump 6 and the venous shut-off clamp 13 are actuated by a central control unit 16 of the dialysis apparatus via control lines 14, 15.

Monitoring of the extra-corporeal blood circuit to detect perivascular bleeding may be performed in the known pieces of blood treating apparatus which operate in what is known as the two-needle mode where there are an arterial and a venous needle to make the vascular access to the patient and in the known dialysis machines in the single-needle mode where there is only one needle for the arterial and venous accesses to the patient.

The arrangement 17 for detecting perivascular bleeding has a means 18 for measuring the arterial pressure in the arterial segment 5 of the extra-corporeal blood circuit I and the venous pressure in its venous segment 7. The measuring means 18 has an arterial pressure sensor 18A which monitors the pressure in the arterial blood line 5 and a venous pressure sensor 18B which monitors the pressure in the venous blood line 7. The measured values from the pressure sensors 18A, 18B are transmitted to a calculating and analyzing unit 20 of the arrangement 17 for detecting perivascular bleeding via data lines 19A, 19B.

The analyzing and calculating unit 20 has means for calculating a non-linear function of the difference between the arterial or venous pressure p(t) which is measured at the time and a preset reference value $p_{ref}$ by using the following equation:

$$I = f(p(t) - P_{ref})$$ Equation (1)

In the next embodiment the non-linear function is assumed to be as follows. The analyzing and calculating unit 20 has means 20A for calculating the integral I of the value of the $n^{th}$ power of the absolute value of the difference between the arterial or venous pressure p(t) which is measured at the time and a preset reference $p_{ref}$ for the pressure, for a preset interval of time $t_2-t_1$, from the following equation.

$$I = \frac{1}{t_2 - t_1} \int_{t_1}^{t_2} |p(t) \quad p_{ref}|^n \, dt$$ Equation (2)

The values given below can be taken as the reference value $p_{ref}$.

1. $p_{ref}$ may be the upper limiting pressure of the limiting pressure band in the known pressure monitoring.
2. $p_{ref}$ may be the lower limiting pressure of the limiting pressure band in the known pressure monitoring.
3. $p_{ref}$ may be the center (symmetrical or asymmetrical) limiting pressure of the limiting pressure band in the known pressure monitoring.
4. $p_{ref}$ may be the value of the pressure when filtered by a low-pass filter.
5. $p_{ref}$ may be a sliding mean value of the pressure.
6. $p_{ref}$ may be a constant.

The reference value may be preset in various ways. The reference value $p_{ref}$ and/or the exponent n and/or the interval of time $t_2-t_1$ may be entered and preset in the arrangement manually by the user or may be stored in a fixed form in the arrangement or may be automatically calculated and suggested by the arrangement following preset rules.

The analyzing and calculating unit 20 also has means 20B for comparing the integral I with a preset limiting value crit.

$$I \geq crit$$ Equation (3)

The integral I is calculated from equation (2) both for the arterial pressure $p_{art}(t)$ which is measured by the arterial pressure sensor 18A and for the venous pressure $p_{ven}(t)$ which is measured by the venous pressure sensor 18B, the integral $I_{art}$ being compared with the preset arterial limiting value $crit_{art}$ and the integral $I_{ven}$ being compared with the preset venous limiting value $crit_{ven}$.

If the limiting value is exceeded, it is concluded that there is perivascular bleeding.

In laboratory tests, the exponent n=3 has proved particularly beneficial for the power function in equation (2). The larger the value of the superscript n is selected to be, the larger are the values p(t) at a long distance from $p_{ref}$. Basically however, the exponent may also be any other desired intermediate value in the range from 2 to 4.

When perivascular bleeding is detected as a result of the limiting value being exceeded, the analyzing and control unit 20 generates a control signal which the central control unit 16 of the dialysis apparatus receives via a control line 21. The control unit 16 then stops the blood pump 6 and closes the venous shut-off clamp 13, thus interrupting the flow of blood in the extra-corporeal blood circuit I. Consequently, no more blood is able to bleed into the peripheral tissue.

The calculating and analyzing unit 20 also has an alarm unit 22 which is connected to the central control unit 16 of the dialysis apparatus via a control line 23. The alarm unit 22 gives an audio and/or visual alarm if perivascular bleeding is detected.

Figure 2:
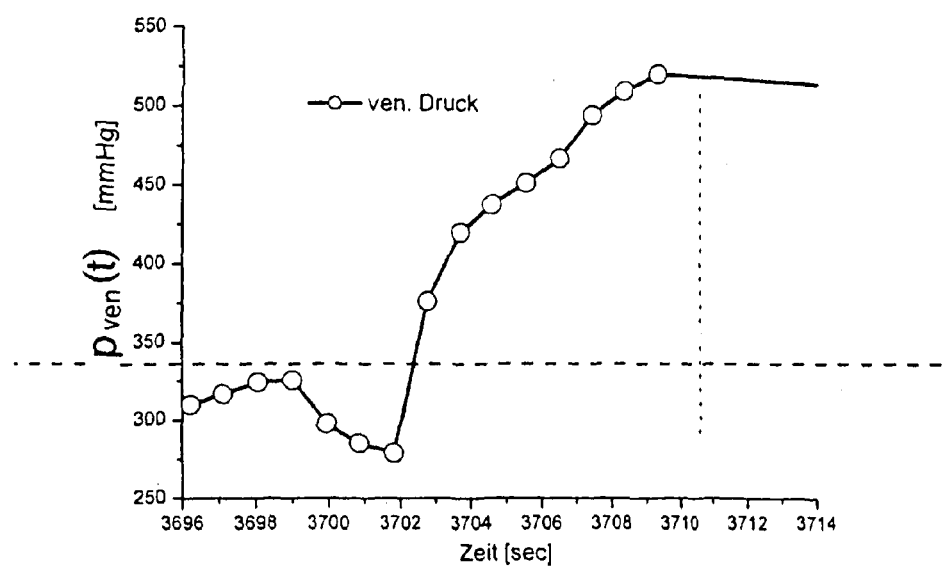
FIG. 2 shows the rise in venous pressure in the venous segment of the extra-corporeal blood circuit when perivascular bleeding occurs.

For conventional pressure monitoring by a known prior art protective system and for the occurrence of perivascular bleeding at the venous needle 7A, FIG. 2 shows the curve followed by the venous pressure $p_{ven}(t)$ in the venous blood line 7, upstream of the venous needle 7A, which is measured by the venous pressure sensor 18B, before and after the occurrence of the perivascular bleeding. A rise in pressure appears when the perivascular bleeding occurs, the venous pressure initially rising slowly and then appreciably faster. The upper limit for the venous pressure, which limit is monitored with the conventional monitoring system, is indicated in FIG. 2 by a dashed line. In the present embodiment it lies at around 330 mmHg. In principle, on the upper limit for venous pressure being reached or exceeded, the blood treatment is interrupted in the case of the conventional monitoring system by the blood pump 6 being stopped and the tube clamp 13 being closed.

However, it can be seen from FIG. 2 that the blood pump is not stopped until approximately t=3711 s, even though the known upper limiting value, which is indicated in FIG. 2 by a dashed horizontal line, has already been exceeded for approximately 9 s. The reason for this is that the conventional protective system in the dialysis apparatus makes provision for a delayed reaction in the form of fixed preset alarm window so that the interruption of the flow of blood only takes place after a preset delay. With the usual blood flows, around 120 ml of blood may be pumped during this time, i.e. when perivascular bleeding is detected as a result of the upper limiting value being exceeded, a further 120 ml of blood is still pumped into the patient's tissue. The purpose of this delayed reaction is to bring down the false alarm rate when there are fairly frequent overruns by the pressure, which generally last for only brief periods and are mostly attributable to innocuous causes, i.e. the reaction is not always to be the immediate switching off of the pump. This being the case, there is a conflict of aims in the conventional protective system between the desires for perivascular bleeding, which is relatively rare in practice but has serious consequences, to be detected at an early stage and for the minimizing of false alarms. The present invention therefore assumes that the known protective system will preferably be left in being and that the protective system according to the present invention will operate in parallel with it, whereby the safety and reliability of the monitoring are increased and false alarms are largely avoided.

The invention claimed is:

1. A method of detecting perivascular bleeding when blood is being fed to and/or taken away from a vascular access via at least one line, the pressure being measured in the at least one line, the method comprising:
   determining a value of a non-linear function of the difference between the measured pressure and a preset reference value;
   comparing the value of the non-linear function with a preset limiting value; and
   determining that there is perivascular bleeding based on an exceeding of the limiting value by the value of the non-linear function.

2. The method according to claim 1, further comprising:
   determining an exponentially raised value of the difference between the measured pressure and the preset reference value by raising the difference to an exponential power;
   comparing the exponentially raised value of the difference in pressure with the preset limiting value; and
   determining that there is perivascular bleeding based on an exceeding of the limiting value by the exponentially raised value of the difference in pressure.

3. The method according to claim 1, further comprising:
   determining an exponentially raised value of the absolute value of the difference between the pressure measured in the line and the preset reference value by raising the absolute value to an exponential power;
   comparing the exponential value of the absolute value of the difference in pressure with the preset limiting value; and
   determining that there is perivascular bleeding based on an exceeding of the limiting value by the exponentially raised value of the absolute value of the difference in pressure.

4. A method of detecting perivascular bleeding during an extra-corporeal blood treatment in which blood flows from an arterial vascular access via an arterial segment of an extra-corporeal blood circuit into a blood treatment device and from the blood treatment device via a venous segment of the extra-corporeal blood circuit to a venous vascular access, the arterial pressure in the arterial segment of the extra-corporeal blood circuit and/or the venous pressure in its venous segment being measured, the method further comprising:
   determining at least one of (a) a first value, of a non-linear function of the difference between the arterial pressure which is measured and a preset reference value for the arterial pressure and (b) a second value, of a non-linear function of the difference between the venous pressure which is measured and a preset reference value for the venous pressure;
   at least one of (a) comparing the first value with a first limiting value and (b) comparing the second value with a second limiting value; and
   determining that there is perivascular bleeding based on (a) the first limiting value being exceeded and/or (b) the second limiting value being exceeded.

5. The method according to claim 4, further comprising:
   determining (a) a first exponentially raised value corresponding to the absolute value, raised to a exponential power, of the difference between the measured arterial pressure and a preset reference value for the arterial pressure and/or (b) a second exponentially raised value, corresponding to the absolute value, raised to an exponential power, of the difference between the measured venous pressure and a preset reference value for the venous pressure; and
   at least one of (a) comparing the first exponentially raised value with a first limiting value and (b) comparing the second exponentially raised value with a second limiting value; and
   determining that there is perivascular bleeding based on (a) the first limiting value being exceeded by the first exponentially raised value and/or (b) second limiting value being exceeded by the second exponentially raised value.

6. Method according to claim 4, further comprising:
- determining, over a preset time interval $t_2-t_1$, an exponentially raised value corresponding to the absolute value, raised to an exponential power, of the difference between the measured arterial pressure and a preset reference value for the arterial pressure;
- comparing the exponentially raised value with a preset limiting value; and
- determining that there is perivascular bleeding based on the preset limiting value being exceeded by the exponentially raised value.

7. The method according to claim 4, further comprising:
- determining, over a preset time interval $t_2-t_1$, an integral value in the form of an integral of the absolute value, raised to an exponential power, of the difference between the measured venous pressure and a preset reference value for the venous pressure;
- comparing the integral value with a preset limiting value; and
- determining that there is perivascular bleeding based on the preset limiting value being exceeded by the integral value.

8. The method according to claim 5, wherein (a) the first exponential value corresponds to the absolute value, raised to an exponential power of two, three or four, of the difference between the measured arterial pressure and a preset reference value for the arterial pressure and/or (b) the second exponential value corresponds to the absolute value, raised to an exponential power of two, three, or four, of the difference between the measured venous pressure and a preset reference value for the venous pressure.

9. The method according to claim 5, wherein (a) the first exponential value corresponds to the absolute value, raised to an exponential power of three, of the difference between the measured arterial pressure and a preset reference value for the arterial pressure and/or (b) the second exponential value corresponds to the absolute value, raised to an exponential power of three, of the difference between the measured venous pressure and a preset reference value for the venous pressure.

10. The method according to claim 1, further comprising providing a visual and/or audio alarm in response to the determination of perivascular bleeding.

11. The method according to claim 1, further comprising interrupting the flow of blood in response to the determination of perivascular bleeding.

12. An arrangement for detecting perivascular bleeding when blood is being fed to and/or taken away from a vascular access via at least one line, the pressure being measured in the at least one line, the arrangement for detecting perivascular bleeding including means of measuring the pressure in the at least one line, the arrangement comprising:
- an analyzing and calculating unit configured to (a) determine a non-linear function of the difference between a measured pressure and a preset reference value, (b) compare the value of the non-linear function with a preset limiting value, and (c) determine that there is perivascular bleeding based on the limiting value being exceeded.

13. The arrangement according to claim 12, wherein the analyzing and calculating unit is further configured to (a) determine an exponentially raised value of the difference between the measured pressure and the preset reference value, (b) compare the exponentially raised value of the difference with the preset limiting value, and (c) determine that there is perivascular bleeding based on the limiting value being exceeded by the exponentially raised value.

14. The arrangement according to claim 12, wherein the analyzing and calculating unit is configured to (a) determine an exponentially raised value corresponding to the absolute value, raised to an exponential power, of the difference between the measured pressure and the preset reference value, (b) compare the exponentially raised value with the preset limiting value, and (c) determine that there is perivascular bleeding based on the limiting value being exceeded by the exponentially raised value.

15. An arrangement for detecting perivascular bleeding during extra-corporeal blood treatment by an extra-corporeal blood treatment apparatus, the extra-corporeal blood treatment apparatus including (a) an arterial blood line belonging to an extra-corporeal blood circuit, which arterial blood line is connected to the inlet of a blood treating means at one end and is provided with an arterial connection for an arterial vascular access at the other end, (b) a venous blood line belonging to the extra-corporeal blood circuit, the venous blood line being connected to the outlet of the blood treating means at one end and is provided with a venous connection for a venous vascular access at the other end, and (c) means for measuring the arterial pressure in the arterial segment of the extra-corporeal blood circuit and/or the venous pressure in its venous segment, the arrangement comprising:
- an analyzing and calculating unit configured to (a) determine a first value, of a non-linear function of the difference between the measured arterial pressure and a preset reference value for the arterial pressure and/or determine a second value, of a non-linear function of the difference between the measured venous pressure and a preset reference value for the venous pressure, (b) compare the first value with a first preset limiting value and/or compare the second value with a second preset limiting value, and (c) determine that there is perivascular bleeding based on the first limiting value and/or the second limiting value being exceeded.

16. The arrangement according to claim 15, wherein the analyzing and calculating unit is configured to (a) determine a first exponentially raised value corresponding to the absolute value, raised to an exponential power, of the difference between the measured arterial pressure and a preset reference value for the arterial pressure and/or determine a second exponentially raised value corresponding to the absolute value, raised to an exponential power, of the difference between the measured venous pressure and a preset reference value for the venous pressure, (b) compare the first exponentially raised value with a first preset limiting value and/or compare the second exponentially raised value with a second preset limiting value, and (c) concluding that there is perivascular bleeding based on the first limiting value being exceeded by the first exponentially raised value and/or the second limiting value being exceeded by the second exponentially raised value.

17. The arrangement according to claim 16, wherein the analyzing and calculating unit includes:
- means for calculating (a) a first integral value, in the form of an integral of the absolute value of the difference between the measured arterial pressure and a reference value for the arterial pressure, over a preset interval of time $t_2-t_1$, and/or (b) a second integral value, in the form of an integral of the absolute value of the difference between the measured venous pressure and a reference value for the venous pressure, over a preset interval of time $t_2-t_1$, and
- means for comparing the first integral value with a first preset limiting value and/or the second integral value with a second preset limiting value.

18. The arrangement according to claim 17, wherein the analyzing and calculating unit is configured to determine (a)

the value, raised to an exponential value of two, three, or four, of the difference between the arterial pressure which is measured and a preset reference value for the arterial pressure or (b) the value, raised to an exponential power of two, three, or four, of the difference between the measured venous pressure and a preset reference value for the venous pressure.

19. The arrangement according to claim 17, wherein the analyzing and calculating unit is configured to determine (a) the value, raised to an exponential power of three, of the difference between the arterial pressure which is measured and a preset reference value for the arterial pressure or (b) the value, raised to the exponential power of three, of the difference between the measured venous pressure and a preset reference value for the venous pressure.

20. The arrangement according to claim 15, further comprising an alarm unit configured to provide a visual and/or audio alarm when the presence of perivascular bleeding is determined.

21. The arrangement according to claim 15, further comprising means for generating a control signal for interrupting the flow of blood in response to the determination of perivascular bleeding.

22. The arrangement according to claim 15, further comprising means for generating a control signal for interrupting the flow of blood in the extra-corporeal blood treating apparatus in response to the determination of perivascular bleeding.

23. An extra-corporeal blood treating apparatus, comprising:
    an arterial blood line of an extra-corporeal blood circuit, the blood line being (a) connected to an inlet of a blood treating means at one end and (b) provided with an arterial connection for an arterial vascular access at the other end,
    a venous blood line of the extra-corporeal blood circuit, the venous blood line being (a) connected to an outlet of the blood treating means at one end and (b) provided with a venous connection for a venous vascular access at the other end, and
    means for measuring (a) the arterial pressure in the arterial segment of the extra-corporeal blood circuit and/or (b) the venous pressure in the venous segment of the extra-corporeal blood circuit, and
    an arrangement according to claim 15.

24. The extra-corporeal blood treating apparatus according to claim 23, further comprising means for interrupting the flow of blood in the extra-corporeal blood circuit.

25. The method of claim 1, wherein the at least one line is a single line, and the measured pressure is the pressure measured in that single line.

26. The arrangement according to claim 12, wherein the at least one line is a single line, and the measured pressure is the pressure measured in that single line.

\* \* \* \* \*